United States Patent [19]

Pronman et al.

[11] 4,302,285
[45] Nov. 24, 1981

[54] NEUTRON ACTIVATION ANALYSIS INSTALLATION

[76] Inventors: Izmail M. Pronman, Leninsky prospekt, 64, kv. 361; Evgeny I. Antonov, 10 Sokolnicheskaya ulitsa, 21, kv. 23; Izrail Y. Barit, ulitsa D. Ulyanova, 3, kv. 96; Anatoly V. Andreev, 1 Naprudnaya ulitsa, 5, kv. 184; Alexandr M. Kazantsev, ulitsa Dezhneva, 9, korpus 2, kv. 214, all of Moscow, U.S.S.R.

[21] Appl. No.: 95,058

[22] Filed: Nov. 16, 1979

[30] Foreign Application Priority Data

Feb. 19, 1979 [SU] U.S.S.R. .................. 2728475
Nov. 23, 1979 [SU] U.S.S.R. .................. 2684301

[51] Int. Cl.$^3$ .......................... G21G 1/06; G01T 1/00
[52] U.S. Cl. ............................................. 376/159
[58] Field of Search ................. 176/10; 250/302–304

[56] References Cited
U.S. PATENT DOCUMENTS 4,053,771  10/1977  Aude et al. ................... 250/303

OTHER PUBLICATIONS

IEEE Trans. on Nuclear Science, vol. NS-22, No. 3, 6/75, pp. 1809–1812.
Ind. Lab. (USA), vol. 38, No. 10, 10/72, pp. 1615–1617.

*Primary Examiner*—Harvey E. Behrend

[57] ABSTRACT

A neutron activation analysis installation comprises a neutron generator whose target chamber communicates through a transport means with a test sample receiving and loading assembly which, in its turn, communicates with a test sample impurity concentration measuring unit. The receiving and loading assembly is in communication with the impurity concentration measuring unit over a channel having a through lateral port communicating on one side with the input of an irradiated sample surface layer removal unit, an irradiated sample distribution assembly being arranged on the other side of the port. The irradiated sample distribution assembly represents an air cylinder with a hollow rod having a bar arranged along the axis thereof and mounting on its end a sample receiver. The bar is disposed in a manner allowing its rotation about the longitudinal axis thereof and reciprocating motion through the port in the channel.

4 Claims, 6 Drawing Figures

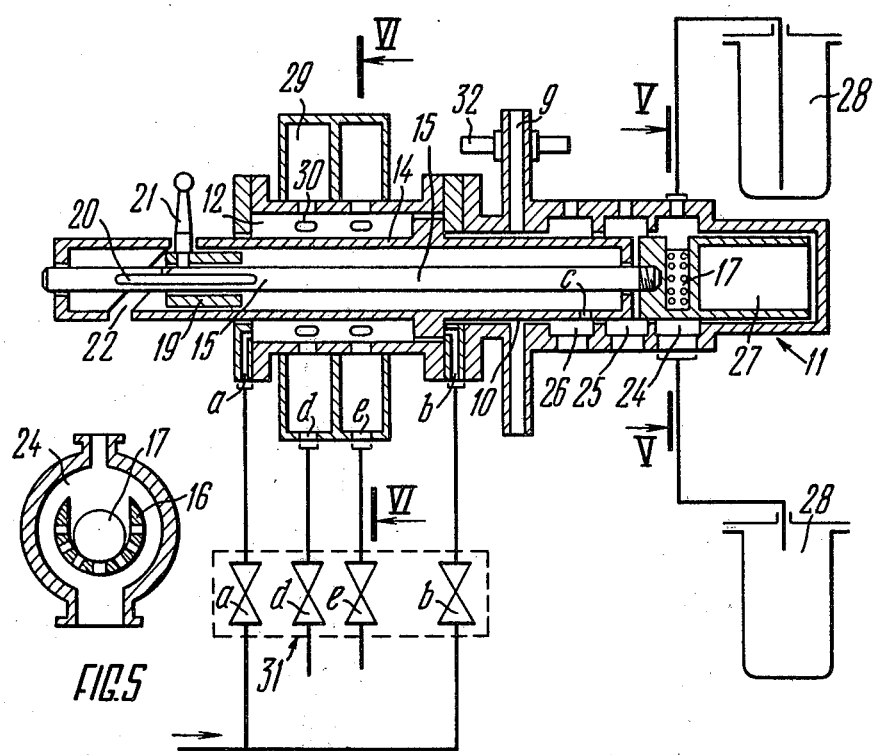
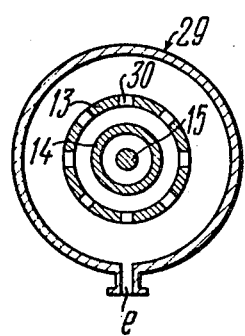
FIG.5
FIG.4
FIG.6

NEUTRON ACTIVATION ANALYSIS INSTALLATION

FIELD OF THE INVENTION

The present invention relates to highly sensitive nuclearphysical means for quantitative determination of an impurity content in various materials, more specifically, for determination of content of lightweight elements and gas impurities such as oxygen, nitrogen, silicon and the like; in particular it concerns neutron activation analysis installations.

The invention may be used at metallurgical and chemical plants, at general metallurgy and machine-building factories, in various branches of industry such as aviation, electronics and the like, as well as in agriculture. It may also be used to advantage for research in solid-state physics and material studies and in monitoring of semi-finished products. Use of aluminum, magnesium and their alloys as well as oxygen-free copper and titanium-magnesium alloys is preferable in the production of lightweight metals and alloys. Use of niobium, molibdenum, tantalum, tungsten, rhenium and like elements as well as special steels and alloys is preferable in the production of refractory and heat-resistant metals.

PRIOR ART

Known in the art are neutron activation analysis installations (cf. J. L. Duggan and I. L. Morgan "Industrial Applications of Small Accelerators", IEEE Transactions on Nuclear Science, 1975, NS-22, No. 3, pp 1216-1228) comprising a neutron generator whose target chamber communicates through a transport means with a test sample receiving and loading assembly which, in its turn, communicates with a test sample impurity concentration measuring unit. Such installations are used for quick determination of impurities, primarily, oxygen whose minimum concentration in the material is $5 \cdot 10^{-3}\%$ by mass. Materials having such an oxigen content may not be regarded as pure or highly pure. The known neutron activation analysis installations may not be used with pure and highly pure materials having an oxigen content of $1 \cdot 10^{-3}\%$ by weight, maximum, a disadvantage associated with the fact that the surface of test samples is contaminated before or during the analysis.

The test sample surface contamination, say, whith oxigen may be due to its sorption from the atmosphere (or vacuum medium), moisture or oil vapour condensation and mechanical impurities from transport means.

For example, the test sample surface may be heavily contaminated due to the injection of $16_N$ recoil nuclei in oxygen determination via the $16_{O(n,p)}16_N$ reaction from the atmosphere and the surface of object adjacent the sample during irradiation. The formed $16_N$ radioactive recoil nucleus acquires kinetic energy sufficient to get onto the surface of the irradiated sample. A maximum energy of the $16_N$ recoil nucleus is 1.8 MeV, the path in metals being 1.5 to $2\mu$, while the path in the air is 4.4 mm. This activity source characterizes an imaginary quasi-oxygen content and not an actual oxygen content in the sample insofar as no difference can be made between the imaginary and actual oxygen in registration of the $16_N$ activity. It is obvious that any treatment of the sample surface before irradiation does not exclude the effect of surface contamination on the analysis results. Also, in the event of sample surface removal after irradiation account should be taken of the total time spent on the treatment of the irradiated sample in contamination removal in view of the fact that a determination sensitivity may be degraded. Since the half life of the $16_N$ isotope is 7.14 s, the sample surface treatment time should not exceed 1 to 1.5 half-life periods, i.e., it should be 10 s, maximum.

Another known method involves the etching of irradiated samples in an aggressive medium for surface removal in doing oxygen content neutron activation analysis (cf. F. Dugain, M. Andre, A. Speecke "Radiochemical Radioanalytical Letters", 4, 121, 35, 1970). With the aforesaid method, the samples are etched manually by performing the following steps: placing the irradiated sample in a vessel containing an etching solution; holding the sample in the vessel as long as needed; removing the etched sample from the vessel; and transferring it into a vessel containing water for washing. The total treatment time amounts, in this case, to 20-30 s.

Serious disadvantages of the aforesaid method are manual etching, a rather long sample treatment time, an increased radiation hazard, sample etching in still water causing sorption of radioactive nuclei from the etching solution, and also incomplete removal of the etching solution from the sample surface.

Also known in the art is a neutron activation analysis installation for determining an oxygen content in highly pure substances (cf. USSR Inventor's Certificate No. 409,555 filed in 1973). As distinct from the aforementioned installation it includes an additional device by means of which the sample is etched after irradiation from a neutron generator. This additional device (irradiated sample surface layer removal unit) represents a rectangular teflon unit having four successively arranged vertical dead channels communicating with one another through guide cavities (slips) whose number suits the number of reagents required to treat the sample. The extreme channels are, respectively, provided whith sample inlet and outlet ports. Connections are incorporated in the channels to deliver the reagents. The vertical channels contain cylindrical pistons with receiving frames on ends thereof, into which the irradiated sample is successively rolled. The pistons with frames are lifted by two air cylinders which are connected in pairs to the respective pistons.

The aforesaid installation has been generally unsatisfactory due to the fact that a rather long time is spent while the irradiated sample moves from the inlet port via all the channels to the outlet port, a limitation resulting in low response and intolerable sample activity loss, which, in its turn, drastically degrades the determination sensitivity. Moreover, the known installation does not permit analyzing conventional samples whithout etching insofar as no provision is made therein for direct communication between the test sample receiving and loading assembly and the impurity concentration measuring unit bypassing the irradiated sample surface layer removal unit. Also, the known installation has been open to the objection that its reliability is comparatively low because of the need to use several moveable cylinders with frames alternately receiving the sample and difficulties encountered in making the frames moving in a boiling acid mechanically strong. The sample is moved from one channel to another over slips filled with reagents by gravity, a limitation preventing the analysis of randomly shaped samples whose density is close to 1 $g/cm^3$.

BRIEF DESCRIPTION OF THE INVENTION

It is an object of the present invention to expand a concentration measurement range by the use of a neutron activation analysis installation.

Another object of the invention is to enhance an impurity determination sensitivity.

A further object of the invention is to reduce a sample treatment time after irradiation.

A still further object of the invention is to improve the construction of a neutron activation analysis installation with a view to increasing its reliability.

The foregoing objects are accomplished by that in a neutron activation analysis installation comprising a neutron generator whose target chamber communicates through a transport means with a test sample receiving and loading assembly communicating, in its turn, with a test sample impurity concentration measuring unit, and also an irradiated sample surface layer removal unit, according to the invention, the receiving and loading assembly is in communication with the impurity concentration measuring unit over a channel having a through lateral port communicating on one side with the input of the irradiated sample surface layer removal unit, an irradiated sample distribution assembly being arranged on the other side of the port, said assembly representing an air cylinder with a hollow shaft having a bar located along the axis thereof and mounting on its end a sample receiver, said bar being disposed in a manner allowing its rotation about the longitudinal axis thereof and reciprocating motion through the port in the channel so that in one extreme position the bar does not reach the channel leaving it vacant, in the intermediate position the sample receiver is found in the channel blocking the latter, and in the other extreme position the sample receiver passes through the port in the channel getting into the surface layer removal unit.

Preferably the mechanism turning the bar about its axis represents a piston contained within a hollow rod encompassing the bar, secured thereon in a manner allowing sliding motion along the latter and coupled to the rod by means of a carrier rigidly connected with the piston and installed in a manner allowing its motion through a screw slot in the rod.

To enhance sensitivity and reliability of the installation, the irradiated sample surface layer removal unit preferably comprises at least three communicating chambers arranged successively in the direction of reciprocating motion of the bar, the position of the last chamber in the direction of progressive motion of the bar corresponding to the extreme position of the bar, while the air cylinder mounts air locks to suit the number of partitions between the communicating chambers.

The neutron activation analysis installation forming the subject of the present invention permits high-accuracy quantitative determination of an impurity and macrocomponent content in various materials, an advantage associated with the fact that the effect of surface contamination on analysis results is excluded. An actual impurity content within the sample is, thus, determined and the probability of a systematic error is substantially reduced.

The hereinproposed installation providing means for impurity determination within a wide concentration range (from tens to $1 \cdot 10^{-5}\%$ by weight) allows its use with conventional initial materials, whether contaminated or highly pure, without any design modifications.

Furthermore, the possibility of analyzing various materials regardless of their properties in solid, powder and liquid phases close to a production site or research ground makes the hereinproposed installation sufficiently versatile to meet production, research and technological needs.

Samples of virtually any shape having an indefinitely low density may be analyzed in the installation forming the subject of the present invention due to the fact that the chambers in the irradiated sample surface layer removal unit are arranged successively in the direction of reciprocating motion of the bar carrying the receiver with the irradiated sample.

BRIEF DESCRIPTION OF DRAWINGS

The invention will be described further with reference to specific embodiments thereof, taken in conjunction with the accompanying drawings, wherein:

FIG. 4 is a longitudinal section similar to FIG. 3 but having an electromagnetic valve system;

FIG. 5 is a section along V—V of FIG. 4, and

FIG. 6 is a section along VI—VI of FIG. 4.

DETAILED DESCRIPTION OF THE INVENTION

Figure 1:
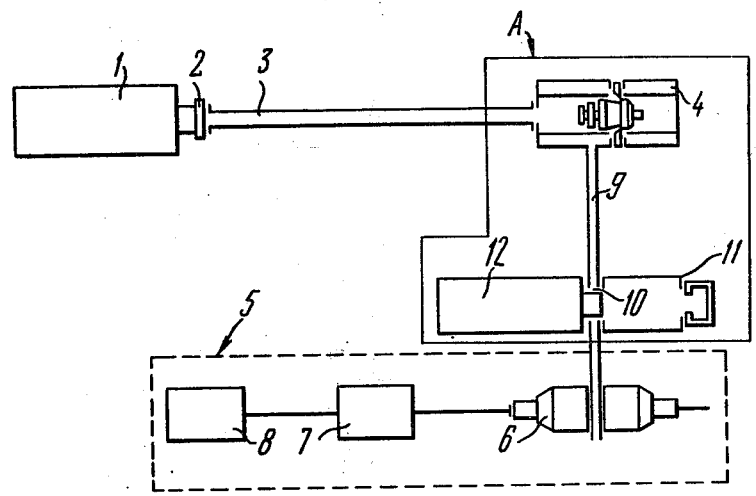
FIG. 1 is a block diagram of a neutron activation analysis installation according to the invention.

Referring to FIG. 1 a neutron activation analysis installation forming the subject of the present invention is designed for quantitative determination of the chemical composition of various materials and quick nondestructive test in the production of metals, alloys, semiconductor and other materials to obtain a desired chemical composition of semi-finished and finished products.

Figure 2:
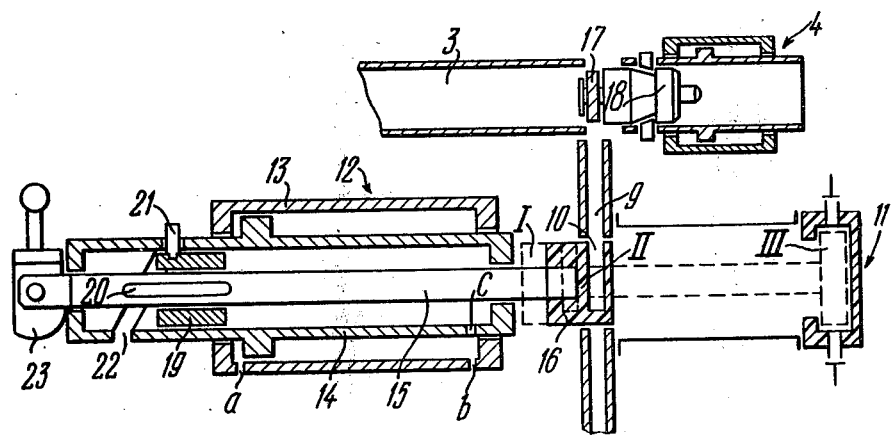
FIG. 2 is an enlarged view of the section A of FIG. 1.

The proposed installation comprises a neutron generator 1 whose target chamber 2 communicates through a transport means 3 with a test sample receiving and loading assembly 4 which, in its turn, communicates with an impurity concentration measuring unit 5. The impurity concentration measuring unit includes a detector 6, measuring equipment 7 and a minicomputer 8 and communicates with the receiving and loading unit 4 over a through channel 9. The channel 9 has a through lateral port 10 communicating on one side with the input of an irradiated sample surface layer removal unit 11, an irradiated sample distribution assembly 12 being arranged on the other side of the port 10, the distribution assembly 12 represents an air cylinder 13 (FIG. 2) with a hollow rod 14 having a bar 15 arranged along the axis thereof, said bar carrying on its end a sample receiver 16. The bar 15 is disposed in a manner allowing its rotation along the longitudinal axis thereof and reciprocating motion through the port 10 in the through channel 9. In one extreme position the bar 15 does not reach the channel 9 (ref. I of FIG. 2 shown with a dashed line) leaving it vacant to enable a sample 17 falling from a capsule 18 (FIG. 2) of the receiving and loading assembly 4 to pass along the through channel 9 into the detector 6 (FIG. 1). In the intermediate position (ref. II of FIG. 2) the sample receiver 16 secured to the bar 15 is found in the channel 9, thus blocking the latter. In the other extreme position (ref. III shown with a dashed line) the bar 15 with the sample receiver 16 gets into the surface layer removal unit 11 after passage via the port 10 in the through channel 9. The reciprocating motion of the bar 15 with the sample receiver 16 and the 180-degree turn of the bar 15 in the through channel 9 are accomplished by supplying air to the air cylinder 13 through holes a and b. Under its pressure the rod 14 with the bar 15 carrying the sample receiver 16 moves in either direction. The bar 15 is turned about its axis by means of a turning mechanism composed of a piston 19 contained within the rod 14 encompassing the bar 15, secured on the bar 15 with a key 20 in a manner allowing sliding motion along the axis of the bar 15 and coupled to the rod 14 by means of a carrier 21 which is rigidly fixed on the piston 19 in a manner allowing its motion through a screw slot 22 in the rod 14. The air displacing the piston 19 is supplied into the cavity of the rod 14 from the air cylinder 13 through a hole "c".

A lever 23 enables installation of the bar 15 in position I or II.

In the event of an oxygen content determination the detector 6 may, for example, represent a device based on two scintillation units with large lead-shielded NaI (T1) crystals.

The measuring equipment 7 may include five discriminating amplifiers, four recomputation devices, and two coincidence circuits. In doing oxygen content analysis, for example, use is made of two sample activity measuring channels, one neutron flux monitoring channel used during irradiation of samples, and one neutron flux test channel.

In doing nitrogen content analysis use is made of five channels and two coincidence circuits.

The minicomputer 8 processing measurement data may include a keyboard computer and a matching unit which interrogates scales, feeds data into the computer and initiates computation instructions in accordance with the preset algorithm.

For example, an oxygen content in the sample in accordance with the preset algorithm is determined from the formula $$\eta_x = \eta_0 \frac{(N_x - N_{1x}) \cdot M_o \cdot m_o \cdot K}{(N_o - N_{1o}) \cdot M_x \cdot m_x} \% \text{ by weight} \quad (1)$$

where $\eta_x$ = oxygen content in the test sample, % by weight;
$\eta_0$ = oxygen content in the reference sample, % by weight;
$N_x$ = number of counts for the sample;
$N_{1x}$ = number of background counts for the sample;
$N_0$ = number of counts for the reference sample;
$N_{10}$ = number of background counts for the reference sample;
$M_x$ = number of sample monitor counts;
$M_0$ = number of reference sample monitor counts;
$M_x$ = weight of the sample, g;
$M_0$ = weight of the reference sample, g; and
K = coefficient accounting for a difference in absorption of $^{16}N$ isotope gammas in the test and reference samples.

Figure 3:
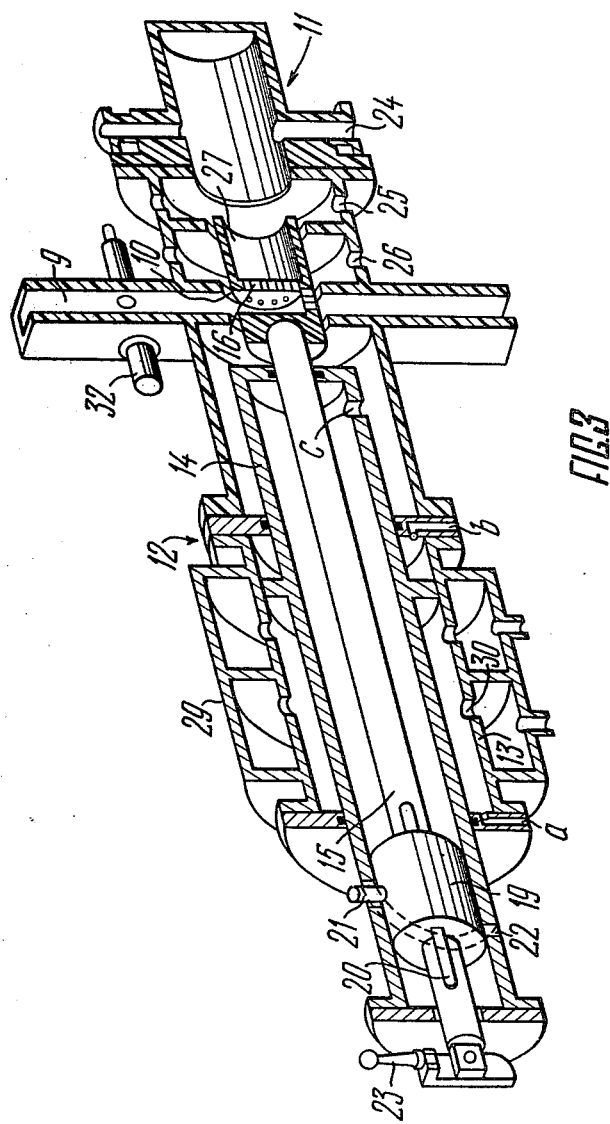
FIG. 3 is a perspective sectional view of an irradiated sample distribution assembly with a surface layer removal unit and a portion of a channel according to the invention.

For clarity, FIG. 3 presents a perspective view of the irradiated sample distribution assembly 12 with the surface layer removal unit 11 and a portion of the channel 9.

Turning now to FIG. 4 the irradiated sample surface layer removal unit 11 comprises at least three communicating chambers 24, 25, 26 arranged successively in the direction of reciprocating motion of the bar 15, the position of the last chamber 24 corresponding to extreme position III of the bar 15. The sample receiver 16 is protected by a cylindrical guard 27 to preclude the penetration of a reagent from one of the chambers (24 to 26) to the other during backward motion of the bar 15. Two vessels 28 containing the reagents are provided for each chamber (24 to 26), one vessel being used to treat the sample with a required reagent, while the other vessel is used for draining the reagent. The air cylinder 13 is provided with air locks 29 whose cavities communicate with the cavity of the air cylinder 13 through ports 30 disposed along the periphery thereof. The number of the air locks 29 suits the number of partitions between the chambers 24 to 26, each lock being designed to brake and stop the bar 15 with the sample receiver 16 in one of the chambers (25 or 26) during its backward motion by discharging the air through outlet connections d, e, respectively. The ports a, b and connections d, e are closed and opened by electromagnetic valves 31 a, b, d and e (letter designations of the valves correspond to letter designations of the respective holes). The operation of the valves 31 is controlled by a timer (not shown in the drawings) activated on signals from a photosenser 32 arranged in the channel 9.

Referring to FIG. 5 the sample 17 is contained within the receiver 16 placed in one of its extreme position in the chamber 24.

In FIG. 6 the ports 30 are distributed along the periphery of the air cylinder 13 and the air lock 29 is shown with the outlet connection e.

The neutron activation analysis installation forming the subject of the present invention operates in the following manner.

Before operation, it is necessary to estimate the purity of the test sample 17 as regards an impurity content. If the impurity content has a concentration exceeding $5 \cdot 10^{-3}\%$ by weight and no surface removal is required after irradiation prior to measuring the sample activity, the lever 23 should be set to position I so that the through channel 9 is unblocked to allow passage of the sample to the detector 6.

The test sample 17 is enclosed in the capsule 18 which is then placed in the receiving and loading assembly 4. The transport means 3 is used to deliver the sample 17 from the receiving and loading assembly to the target chamber 2 of the neutron generator 1 wherein the sample 17 is irradiated. The same transport means 3 delivers the irradiated sample 17 to the receiving and loading assembly 4 whence it goes over the through channel 9 to the detector 6. The sample activity is measured by the measuring equipment 7, the impurity content is calculated from formula (1) using the minicomputer 8 and a presentation of the result is provided.

If the sample 17 is pure or highly pure having, for example, an oxygen content less than $5 \cdot 10^{-3}\%$ by weight, the lever 23 should be set to position II so that the sample receiver 16 blocks the through channel 9. The transport means 3 delivers the sample 17 with the capsule 18 to the target chamber 2 of the neutron generator 1 wherein it is irradiated. At a preset time after irradiation the transport means 3 delivers the sample 17 with the capsule 18 to the receiving and loading assembly 4. Therefrom the sample 17 removed from the capsule 18 passes over the through channel 9 to the sample receiver 16. As the sample 17 passes over the channel 9, the photosensor 32 furnisches a signal causing the electromagnetic valve 31 a to open. From said valve the compressed air is supplied through the port a to the air cylinder 13, thus pushing the rod 14 with the internal bar 15 whose end mounts the receiver 16 with the sample 17 via the through port 10 into the irradiated sample surface layer removal unit 11. The receiver 16 with the sample 17 is placed in the extreme chamber 24 under the inlet connection coupled to the vessel 28 filled with the reagent required to treat the irradiated sample 17 with a view to removing its surface layer. When the receiver 16 is installed in the chamber 24, the running reagent in a uniform manner the surface layer from the irradiated sample 17 after which it is drained into the second vessel 28 through the outlet connection. At a preset time after the treatment of the sample in the chamber 24 is completed the compressed air is supplied through the open electromagnetic valve 31b and the respective port b to the air cylinder 13, thus pushing the rod 14 with the bar 15 and the receiver 16 which is stopped in the next chamber 25 to enable further treatment or washing of the sample 17 in the receiver 16 with running reagent or water. As this happens, the guard 27 closes the port through which the chambers 24 and 25 communicate. To stop the receiver in the chamber 25, the rod 14 is braked by discharging the air from the air lock 29 through the connection e and the electromagnetic valve 31e. At a preset time after the treatment of the sample 17 in the chamber 25 is completed, the valve 31e closes and the air coming through the port b pushes the rod 14 until the receiver 16 with the sample 17 stops in the chamber 26 to enable further treatment and blowing of the sample 17 with air. The receiver 16 with the sample 17 is stopped in the chamber 26 by discharging the air from the second air lock 29 through the connection d and the electromagnetic valve 31g. In this case, the guard 27 closes the two ports through which the chambers 24 to 26 communicate. At a preset time after the treatment of the sample 17 in the chamber 26 is completed, the valve 31d closes and and the compressed air is supplied through the valve 31b and the port b to the air cylinder 13, thus pushing the rod 14 until the receiver 16 with the sample 17 enters the through channel 9. When the receiver 16 with the sample 17 is placed in the through chanel 9, the compressed air is supplied from the air cylinder 13 through the port c to the cavity of the rod 14, thus pushing the piston 19 which slides along the axis of the bar 15. Since the piston 19 is coupled to the rod 14 by means of the carrier 21 rigidly fixed on the piston 19 in a manner allowing its motion through the screw slot 22 in the rod 14, the bar 15 with the sample receiver 16 makes a 180-degree turn thanks to the screw slot 22 whereby the sample 17 is removed from the receiver 16 and supplied to the detector 6 over the through channel 9. Next, the sample activity is measured by the equipment 7 and the minicomputer comutes in accordance with the preset algorithm (say, formula (1) an oxygen content and feeds the test data to a printer or a display unit. The minicomputer also allows computing errors of a randomly chosen set of data or a single test.

The entire impurity determination process is invariably short, say, from 1.5 to 3 min in doing oxygen content analysis, its duration being dependent upon the half-life of a given radioisotope.

A short impurity determination time permits monitoring the entire process of fabricating semi-finished products to a high accuracy.

Another advantage of the proposed neutron activation analysis installation over the prior art is that it holds much promise as regards sensitivity, accuracy, use of a still greater number of elements for impurity content analysis, automation of the entire test process and fast data output by sound signalling, visual presentation or printing. The aforesaid advantage is associated with the use of a high-current neutron generator with a minimum flux of $5 \cdot 10^{12}$ neutron/s employing deuterium-tritium beams and a tritium-fed target and also of a minicomputer and up-to-date integrated circuits, which is generally a space-saving factor allowing further miniaturization. Using neutron moderators the herein-proposed installation is capable of operating not only with direct-action accelerators generating monochromatic ~14 MeV neutrons but also with slow and thermal reactors. Furthermore, the installation forming the subject of the present invention makes it possible to do volume, surface and correlation analyses.

What is claimed is:

1. A neutron activation analysis installation comprising: a neutron generator, a target chamber of said neutron generator; a receiving and loading assembly; a transport means communicating said receiving and loading assembly with said target chamber; a test sample impurity concentration measuring unit; a through channel communicating said impurity concentration measuring unit with said receiving and loading assembly; a through lateral port in said channel; an irradiated sample surface layer removal unit located against said port on one side of said channel; an irradiated sample distribution assembly disposed against said port on the opposite side of said channel with respect to said surface layer removal unit; an air cylinder being the main part of said irradiated sample distribution assembly; a hollow rod in said air cylinder; a bar arranged along the axis of said hollow rod; a sample receiver rigidly fixed on the end of said bar; said bar disposed in a manner allowing its rotation about the longitudinal axis thereof and reciprocating motion through said port in said channel so that in one extreme position said bar does not reach said channel leaving it vacant, in the intermediate position of said bar said sample receiver is found in said channel blocking the latter and in the other extreme position of said bar said sample receiver passes through said port in said channel and gets into said surface layer removal unit.

2. An installation as claimed in claim 1, wherein a mechanism turning said bar about the axis thereof comprises: a piston contained within said hollow rod encompassing said bar and secured thereon in a manner allowing sliding motion along the latter; a screw slot in said rod; a carrier rigidly connected with said piston and installed in a manner allowing its motion through said slot.

3. An installation as claimed in claim 1, wherein said surface layer removal unit includes at least three communicating chambers arranged successively in the direction of reciprocating motion of said bar; the position of the last chamber in the direction of progressive motion of said bar corresponding to said extreme position of said bar: the member of the air locks arranged on the air cylinder being less by one than the number of said chambers.

4. An installation as claimed in claim 2, wherein said irradiated sample surface layer removal unit includes at least three communicating chambers arranged successively in the direction of reciprocating motion of said bar; the position of the last chamber in the direction of progressive motion of said bar corresponding to said extreme position of said bar; the number of the air locks arranged on the air cylinder being less by one than the number of said chambers.

* * * * *